(12) United States Patent
Astrup et al.

(10) Patent No.: US 7,867,526 B2
(45) Date of Patent: Jan. 11, 2011

(54) COMPOSITION FOR WEIGHT REDUCTION COMPRISING CAPSAICIN, GREEN TEA EXTRACT, L-TYROSINE AND CAFFEINE

(75) Inventors: Arne Vernon Astrup, Klampen Borg (DK); Soren Toubro, Vipperod (DK)

(73) Assignee: Ideasphere, Inc., American Fork, UT (US)

( * ) Notice: Subject to any disclaimer, the term of this patent is extended or adjusted under 35 U.S.C. 154(b) by 0 days.

(21) Appl. No.: 11/901,089

(22) Filed: Sep. 14, 2007

(65) Prior Publication Data

US 2008/0008770 A1 Jan. 10, 2008

Related U.S. Application Data

(63) Continuation of application No. 11/112,699, filed on Apr. 21, 2005, now abandoned.

(51) Int. Cl.
*A61K 36/82* (2006.01)
*A61K 36/81* (2006.01)
*C07D 473/00* (2006.01)

(52) U.S. Cl. .................... 424/729; 424/760; 544/274
(58) Field of Classification Search .................. None
See application file for complete search history.

(56) References Cited

U.S. PATENT DOCUMENTS

| 4,812,446 | A |   | 3/1989  | Brand           |
|-----------|---|---|---------|-----------------|
| 5,273,754 | A | * | 12/1993 | Mann ........... 424/440 |
| 5,290,816 | A |   | 3/1994  | Blumberg        |
| 6,277,396 | B1| * | 8/2001  | Dente ........... 424/439 |
| 2004/0180077 | A1 |   | 9/2004 | Riker et al.    |

FOREIGN PATENT DOCUMENTS

JP         2000189108 A  *  7/2000
WO      WO 0041708 A1  *  7/2000

OTHER PUBLICATIONS

BioQuest Tetrazine ES-50. Internet Archive Date: Feb. 5, 2005 [Retrieved from the Internet on: Jan. 8, 2008]. Retrieved from: http://web.archive.org/web/*/http://www.bodybuilding.com/store/bioq/tet50.html.*
"Caffeine". Internet Archive Date: Apr. 22, 2001 [Retrieved from the Web on: Sep. 13, 2008] Retrieved from: <http://web.archive.org/web/20010422225225/http://www.stanford.edu/~johnbrks/theCafe/substance/caffeine.html>.*
Murase et al. "Beneficial effects of tea catechins on diet-induced obesity: Stimulation of lipid catabolism in the liver". International Journal of Obesity. vol. 26 (2002) 1459-1464.*
(U1) "Bodybuilding.com: Now L-Tyrosine". Internet Archive Date: Apr. 4, 2004 [Retrieved from the Internet on: Apr. 2, 2010]. Retrieved from: <http://web.archive.org/web/20040404123738/www.bodybuilding.com/store/now/lty.html>.*

Tsi et al. "Clinical study on the combined effect of capsaicin, green tea extract and essence of chicken on body fat content in human subjects". J. Nutr. Sci. Vitaminol. (Tokyo) vol. 49, No. 1 (Dec. 2003)) 437-441.*
Preuss H.G., et al., 2002, Citrus aurantium as a thermogenic, weight-reduction replacement for ephedra: an overview, J. Med., 33(1-4):247-64.
Remington's Pharmaceutical Sciences, 1980, 16th Ed. Mack Publishing Company, Eason, USA.
Szallasi A., & Blumberg P.M., 1990, Resiniferatoxin and its analogs provide novel insights into the pharmacology of the vanilloid (capsaicin) receptor, Life Sci. 47(16):1399-408.
Tsi D. Nah, AK, Kiso Y, Moritani T., Ono H. PubMed Abstract J Nutr Sci Vitaminol (Tokyo). 2003; 49(6): 437-441.
Vogel G, 2000, Hot pepper receptor could help manage pain, Science. 288: 241-242.
Yoshioka M., et al., 1995, Effects of red-pepper diet on the energy metabolism in men, J Nutr Sci Vitaminol. 41: 647-656.
Yoshioka M., et al., 1998, Effects of red pepper added to high-fat and high-carbohydrate meals on energy metabolism and substrate utilization in Japanese women, Br. J. Nutr. 80: 503-510.
Yoshioka M., et al., 1999, Effects of red pepper on appetite and energy intake, Br. J. Nutr. 82: 115-123.
http://web.archive.org/web/*/http://www.bodybuilding.com/store/4yh/burn.html(Web Publication Date: Dec. 4, 2003). Date Accessed: Nov. 9, 2006.
http://web.archive.org/web/*/http://www.bodybuilding.com/store/mt/hydroxyef.html(Web Publication Date: Mar. 3, 2003). Date Accessed: Nov. 9, 2006.
Astrup, A. et al., 1990, Prediction of 24 h energy expenditure and its components from physical characteristics and body composition in normal-weight humans. Am. J. Clin. Nutr. 52:777-83.
Astrup A, 1986, Thermogenesis in human brown adipose tissue and skeletal muscle induced by sympatomimetic stimulation, Acta Endocrinol 112, supp 278:1-32.
Belza, A., & Jessen, A.B., 2005, Bioactive food stimulants of sympathetic activity: effect on 24-h energy expenditure and fat oxidation, Eur J Clin Nutr. 59(6):733-41.
Bligh, E.G., & Dyer, W.J., 1959, A rapid method of total lipid extraction and purification. Can. J. Biochem. Physiol. 37: 911-7.
Caterina MJ., et al., 2000, Impaired nociception and pain sensation in mice lacking the capsaicin receptor, Science. 288: 306-313.
Council on Scientific Affairs, 1988, Treatment of obesity in adults, JAMA 260:2547-48.

(Continued)

*Primary Examiner*—Amy L Clark
(74) *Attorney, Agent, or Firm*—The Nath Law Group; Laurie A. Axford

(57) ABSTRACT

A composition for reducing the weight of a human. The composition is provided in the form of a capsule comprising an effective amount of capsaicin and/or analogs thereof, L-tyrosine, supplemental caffeine and/or and analogs thereof, green tea extract containing catechin and caffeine, and embodiments which include calcium. The invention is also directed toward methods for reducing and maintaining weight of a human using the composition.

2 Claims, 4 Drawing Sheets

OTHER PUBLICATIONS

Dulloo, A. & Miller, D.S., 1989, Ephedrine, caffeine and aspirin: "Over-the-counter" drugs that interact to stimulate thermogenesis in the obese, Nutrition 5:7-9.

Dulloo AG, et al., 1994, Paraxanthine (metabolite of caffeine) mimics caffeine's interference with sympathetic control of thermooenesis, Am J Physiol, 267:E801-4.

Hill, A.J., et al., 1984, Hunger and palatability: tracking ratings of subjective experience before, during and after the consumption of preferred and less preferred food, Appetite 5:361-71.

Hill, J.O., et al., 2003, Obesity and the environment: where do we go from here, Science 299:853-5.

Hollands, M.A., et al, 1981, A simple apparatus for comparative measurements of energy expenditure in human subjects: the thermic effect of caffeine, Am. J. Clin, Nutr. 34:2291-4.

Hull, K.M. & Mahar, T.J., 1990, L-tyrosine potentiates the anorexia induced by mixed-acting sympathomimetic drugs in hyperphagic rats, J. Pharmacol. Exp.Thereapeutics 255(2):403-9.

Jacobsen, R., et al, 2005, Effect of short-term high dietary calcium intake on 24-h energy expenditure, fat oxidation, and fecal fat excretion, Intl J. Obesity 29, 292-301.

Klausen B., et al. 1997, Age and sex effects on energy expenditure, Am. J. Clin. Nutr. 65:895-907.

Korel, F., et al., 2002, Ground red peppers: capsaicinoids content, Scoville scores, and discrimination by electronic nose, J. Agric. Food Chem., 50: 3257-3261.

Lejeune MPGM., et al., 2003, Effect of capsaicin on substrate oxidation and weight maintenance after modest body-weight loss in human subjects, Br. J. Nutr. 90: 651-9.

Lim K., et al., 1997, Dietary red pepper ingestion increases carbohydrate oxidation at rest and during exercise in runners. Med. Sci. in. Sports Exerc. 29: 355-361.

Lorenzen et al., 2006, Calcium supplementation for 1 y does not reduce body weight or fat mass in young girls, Am J. Clin. Nutr., 83: 18-23.

Masuda Y., et al., 2003, Upregulation of uncoupling proteins by oral administration of capsiate, a nonpungent capsaicin analog, J. Appl. Physiol. 95(6):2408-15.

* cited by examiner

A
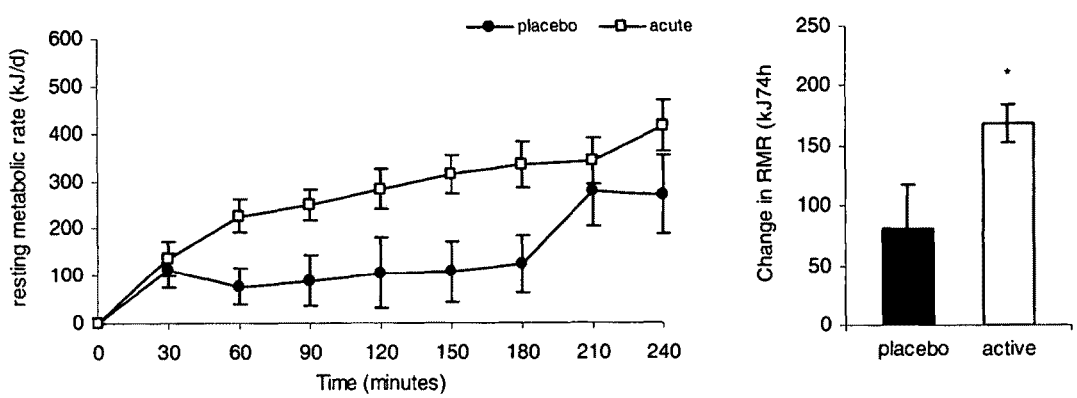
B
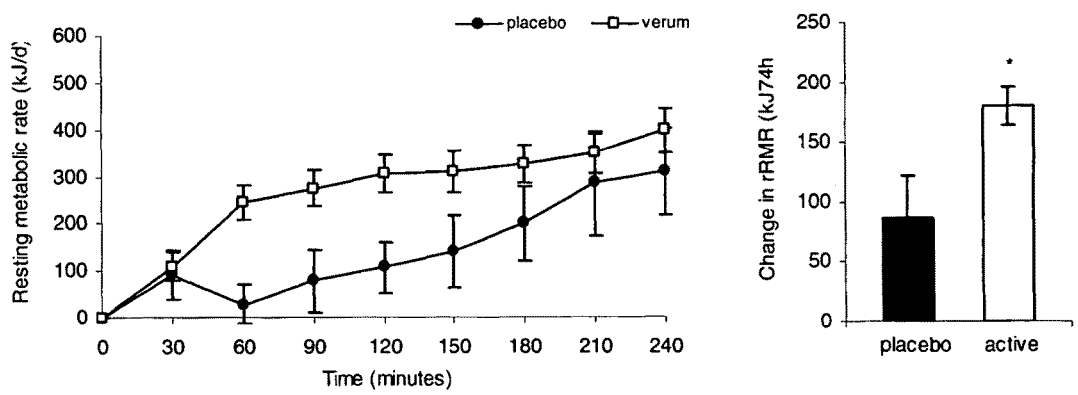
FIGURE 3 A & B

Change in RMR (kJ/4h)

COMPOSITION FOR WEIGHT REDUCTION COMPRISING CAPSAICIN, GREEN TEA EXTRACT, L-TYROSINE AND CAFFEINE

CROSS REFERENCE TO RELATED APPLICATION

This application is a continuation application of application Ser. No. 11/112,699, filed Apr. 21, 2005.

FIELD OF THE INVENTION

The invention relates to a composition to reduce weight and maintain weight loss in overweight or obese individuals, and inhibit weight gain after weight loss. The composition comprises, capsaicin, tyrosine, supplemental caffeine, green tea extract, which comprises catechin and caffeine, and embodiments which include calcium. The invention is further directed to a method of using the composition for weight loss and for maintenance of weight loss.

BACKGROUND OF THE INVENTION

Overweight and Obese Populations

Prosperous, industrialized countries have a large number of overweight or obese populations. More than half of the adults in the US are overweight (61%) and more than a quarter (26%) are obese. A person who is overweight or obese has an excessive accumulation of fat in the body. One way that excessive accumulation of fat can occur is through consumption of a diet with an energy intake which is greater than the energy expenditure of the body. It is generally agreed that a person is overweight if their body weight exceeds their "desirable weight", whereas obesity is present if the body weight is 20% or more above the "desirable weight" (Council on Scientific Affairs, 1988, Treatment of obesity in adults, *JAMA* 260:2547-48). Body mass index (BMI) is a common measure expressing the relationship (or ratio) of weight-to-height. It is a mathematical formula in which a person's body weight in kilograms is divided by the square of his or her height in meters (i.e., $wt/(ht)^2$). The BMI is more highly correlated with body fat than any other indicator of height and weight. Individuals with a BMI of 25 to 29.9 are considered overweight, while individuals with a BMI of 30 or more are considered obese. According to the NIH Clinical Guidelines on the Identification, Evaluation, and Treatment of Overweight and Obesity in Adults, all adults (aged 18 years or older) who have a BMI of 25 or more are considered at risk for premature death and disability as a consequence of overweight and obesity. These health risks increase as the severity of an individual's obesity increases.

Obesity can be further classified as mild (20-30% overweight), moderate (30-60% overweight) or severe ($\geq 60\%$ overweight). A number of health hazards correlate with moderate and severe obesity, including impairment of both cardiac and pulmonary functions, perturbation of endocrine functions, emotional problems, hypertension, impaired glucose tolerance, non-insulin dependant diabetes mellitus, and hypercholesterolemia. Colonic and rectal cancer are diseases which frequently appear in obese men, and obese women often suffer from endometrial or gallbladder cancer.

The causes of obesity are complex and not fully understood. Obesity can be a result of life-style (i.e. patterns of physical activity and food consumption), or a result of individual genetic propensity.

Methods of Treatment for Weight Loss

The basic principle of treatment of obese or overweight individuals has been establishment of a negative energy balance. A negative energy balance can be accomplished by using one or a combination of three different methods of treatment. The first method of treatment is the reduction of energy intake. This is essentially possible only through dietary treatment, as malabsorption of food cannot be obtained safely either through medication or surgery. The dietary treatment consists of a weight reducing diet as well as a weight maintaining diet.

The second method to achieve a negative energy balance is by an increase in physical activity, which leads to increased energy expenditure. However, in order to obtain a significant amount of weight loss, hours of daily physical activity would be needed. Therefore, physical activity alone plays a minor role in the treatment of obesity but a major role in weight loss maintenance.

The third method to achieve a negative energy balance is through the use of drugs or supplements, either alone or in combination with dietary treatment and/or increased physical activity. The drugs used in the treatment of obesity can be appetite-reducing drugs (sibutramine), drugs that produce malabsorption of fat (orlistat) or carbohydrate (acabose), and thermogenic drugs. A thermogenic drug can be defined as a drug capable of raising the metabolic rate, i.e. increasing the energy expenditure. Known thermogenic drugs are e.g. ephedrine, epinephrine, norepinephrine, isoproterenol, phenylpropanolamin and caffeine (Astrup A., 1986, Thermogenesis in human brown adipose tissue and skeletal muscle induced by sympatomimetic stimulation, *Acta Endocrinol.* 112, suppl 278:1-32; Hollands, M. A., et al, 1981, A simple apparatus for comparative measurements of energy expenditure in human subjects: the thermic effect of caffeine, *Am. J. Clin, Nutr.* 34:2291-4). The interest in thermogenic drugs stems from studies which indicate that obesity might be genetically determined, and that the responsible genetic defect relates to a thermogenic defect of the obese person (Dulloo, A. & Miller, D. S., 1989, Ephedrine, caffeine and aspirin: "Over-the-counter" drugs that interact to stimulate thermogenesis in the obese, *Nutrition* 5:7-9). The term "a thermogenic compound" or "a thermogenically active compound" is understood to mean a compound which is within a living animal capable of raising metabolic rate, i.e. increasing energy expenditure. The term "therapeutically active substance" as used herein is intended to mean any physiologically or pharmacologically active substance that produce a localized or systemic effect in humans.

Treatment of overweight or obese individuals with thermogenic drugs is generally thought to have successful therapeutic value, and as a result there is an interest in the search for new thermogenic compounds.

It has been shown that ephedrine is an effective weight loss agent through its ability to increase thermogenesis and quench appetite. However, the publicity concerning adverse reactions has led to its gradual withdrawal from use. Many companies are now substituting *Citrus aurantium* for ephedrine in their formulations. (Preuss H. G., et al., 2002, *Citrus aurantium* as a thermogenic, weight-reduction replacement for ephedra: an overview, *J. Med.*, 33(1-4):247-64.)

While many of the technologies mentioned above are useful in losing weight, the problem is keeping the weight off. Often people "yo-yo", that is, loose large amounts of weight only to gain it back once they discontinue the weight loss program they were on. A reduction in energy gain by 50 kcal/day could offset weight gain in about 90% of the population. This could theoretically be accomplished by walking an extra mile a day (100 kcal), or simply by eating a few bites less of each meal (Hill, J. O., et al., 2003, Obesity and the environment: where do we go from here, *Science* 299:853-5). Although these simple solutions have been known for many years, the majority of the population is still gaining weight. There is clearly a need for simple and safe methods to achieve satiety and decrease spontaneous food intake, as well as to use safe and effective compounds to increase thermogenesis and lead to weight loss. Therefore, it was of interest to develop a composition containing well-known, harmless food ingredients which achieve a synergistic effect and leads to weight loss.

SUMMARY OF THE INVENTION

This invention is directed to a composition which is administered by an individual for reducing weight. The composition comprises an effective amount of capsaicin and/or analogs thereof, L-tyrosine, green tea extract, supplemental caffeine and/or analogs thereof, and embodiments which include calcium. The green tea extract comprises catechin and caffeine. A preferred embodiment of the composition comprises a pharmaceutically acceptable carrier.

The invention includes a method for reducing the fat mass and body weight of a human. The method involves administration of an effective dose or amount of the composition of the invention. Yet another aspect of the invention is a method of using the composition of the invention for maintaining weight loss by administering effective amounts of the composition after an individual achieves a desired reduction of weight.

BRIEF DESCRIPTION OF THE FIGURES

FIG. 3: Baseline subtracted change in resting metabolic rate (mean±SD) during 4-h measurement in the two subgroups. (A) Acute effect at first exposure of supplement: placebo group (age: 51.0±10.5y, n=23, 4 males) and bioactive group (age: 46.6±11.0y, n=52, 14 males). (B) Subchronic effect of last exposure after 8-week supplementation: placebo group (age: 51.7±10.9y, n=21, 3 males) and active group (age: 47.2±10.8y, n=52, 11 males).

DETAILED DESCRIPTION OF THE INVENTION

Figure 1:
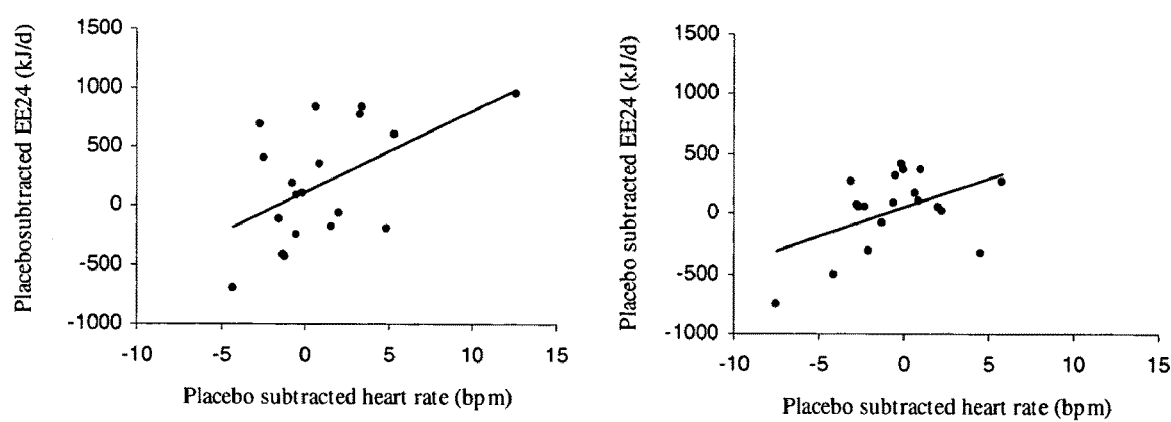
FIG. 1: Relationship between placebo-subtracted estimates of 24-h EE and 24-h heart rate in 19 overweight men. Data analyzed by Pearson correlation: plain release formulation (left: r=0.53, p=0.02) and controlled release formulation (right: r=0.47, p=0.04).

The invention is directed towards a composition with an effective amount of capsaicin and/or analogs thereof, L-tyrosine, supplemental caffeine and/or analogs thereof, green tea extract containing catechin and caffeine, and embodiments which include calcium. The invention is also directed toward a method for weight reduction and weight maintenance with use of the composition.

Tyrosine

L-Tyrosine is a high ranking neurotransmitter amino acid that can stimulate and modify brain activity to reduce hunger and improve memory and mental alertness. Experimental studies suggest that tyrosine may potentiate the effect of ephedrine and other sympathetic nervous system stimulants on energy balance. (Hull, K. M. & Mahar, T. J., 1990, L-tyrosine potentiates the anorexia induced by mixed-acting sympathomimetic drugs in hyperphagic rats, J. Pharmacol. Exp. Thereapeutics 255(2):403-9)

Capsaicin

Capsaicin (CAP) is the major pungent ingredient in fruits of the *Capsicum annuum* L genus, which include red pepper, paprika and chilies, and has been used throughout the world as a spice. CAP are a class of compounds of branched- and straight-chain alkyl vanillylamides. Analogs of CAP's with similar physiological properties are known. (Masuda Y., et al., 2003, Upregulation of uncoupling proteins by oral administration of capsiate, a nonpungent capsaicin analog, *J. Appl. Physiol.* 95(6):2408-15; Szallasi A., & Blumberg P. M., 1990, Resiniferatoxin and its analogs provide novel insights into the pharmacology of the vanilloid (capsaicin) receptor, *Life Sci.* 47(16): 1399-408) For example, resiniferatoxin is described as a CAP analog in U.S. Pat. No. 5,290,816, and CAP analogs and methods for their preparation are described in U.S. Pat. No. 4,812,446, both incorporated herein by reference. It has been shown that CAP added to meals increased SNS activity and EE (Yoshioka M., et al., 1999, Effects of red pepper on appetite and energy intake, *Br. J. Nutr.* 82: 115-123. Yoshioka M., et al., 1998, Effects of red pepper added to high-fat and high-carbohydrate meals on energy metabolism and substrate utilization in Japanese women, *Br. J. Nutr.* 80: 503-510, Lejeune MPGM., et al., 2003, Effect of capsaicin on substrate oxidation and weight maintenance after modest body-weight loss in human subjects, *Br. J. Nutr.* 90: 651-659). However, there are some inconsistencies about the effect of CAP on the substrate oxidation (Yoshioka M., et al., 1995, Effects of red-pepper diet on the energy metabolism in men, *J Nutr Sci Vitaminol.* 41: 647-656. Lim K., et al., 1997, Dietary red pepper ingestion increases carbohydrate oxidation at rest and during exercise in runners. *Med. Sci. in. Sports Exerc.* 29: 355-361). CAP is thought to activate the sympathetic nerves via vanilloid receptor 1 (VR-1) by stimulating the release of NE into the synaptic cleft (Caterina M J., et al., 2000, Impaired nociception and pain sensation in mice lacking the capsaicin receptor, *Science.* 288: 306-313. Vogel G, 2000, Hot pepper receptor could help manage pain, *Science.* 288: 241-242).

CAP is measured in Scoville heat units. The relationship between the concentration of CAP and Scoville heat units has been determined by measuring the concentration of capsaicin by a HPLC method and Scoville heat units with an electronic sensory nose. (Korel, F., et al., 2002, Ground red peppers: capsaicinoids content, Scoville scores, and discrimination by electronic nose, *J. Agric. Food Chem.,* 50: 3257-3261) The formula for determining the Scoville heat units is: 76.8*(CAP mg/100 g *Capsicum annuum* L.)+2691=Scoville heat units. As an example of the calculation, 76.8*(267 mg CAP/100 g cayenne)+2691=23,200 Scoville heat units.

Green Tea

Green tea contains catechin and caffeine. Catechins are flavonoids and have antioxidant properties. Green tea extract rich in the polyphenol catechin epigallocatechin gallate has been shown to increase sympathetic nervous system activity, and to increase 24-h energy expenditure and fat oxidation (Dulloo A G, et al., 1994, Paraxanthine (metabolite of caffeine) mimics caffeine's interference with sympathetic control of thermogenesis, *Am J Physiol,* 267:E801-4)

Methylxanthines are a group of related agents including caffeine, paraxanthine, xanthine and others naturally occurring in numerous food products coffee, tea, the cocoa bean etc. Administration of methylxanthines has only weak biological effects on thermogenesis and appetite, but when given in conjunction with agents stimulating SNS, they are potent amplifiers of thermogenesis in humans. (Dulloo A G, et al., 1994, Paraxanthine (metabolite of caffeine) mimics caffeine's interference with sympathetic control of thermogenesis, *Am J Physiol,* 267:E801-4) Although green tea extract contains caffeine, the composition of the invention contains additional, supplemental caffeine. Thus, the composition provides caffeine in the green tea extract as well as supplemental caffeine.

Calcium

Forms of calcium useful in the composition include calcium bound either in a salt or in an organic compound. Calcium (Jacobsen, R., et al, 2005, Effect of short-term high dietary calcium intake on 24-h energy expenditure, fat oxidation, and fecal fat excretion, *Intl J. Obesity* 29, 292-301). The composition of the invention provides calcium supplementation, regardless of the form in which calcium is furnished to the subject, in the range of 50-8000 mg elementary calcium. The calcium salts useful in the invention include, but are not restricted to, calcium carbonate, calcium sulfate, dibasic calcium phosphate, calcium sodium magnesium phosphate, monodibasic calcium phosphate, dihydrated dibasic calcium phosphate, calcium sodium phosphate. Forms of calcium bound to organic molecules include, but are not restricted to, calcium lactate, calcium fumarate, calcium malate fumarate, calcium citrate, calcium citrate malate, biolactal calcium, calcium formate, calcium lactogluconate/carbonate.

In the present context the term "overweight" is used as an indication of a body with a weight exceeding the "desirable weight", whereas the term "obesity" is used when the body weight is 20% or more above the "desirable weight". Desirable weights for humans are given by the Council on Scientific Affairs defining the desirable weights for humans according to Metropolitan Height and Weight Tables as the midpoint of the range of the medium-frame individuals. (Council on Scientific Affairs, 1988, Treatment of obesity in adults, *JAMA* 260:2547-48.

The term "effective amount" as used herein is intended to mean the amount of the composition administered to achieve and maintain weight loss in an overweight or obese individual. The effective amounts of the agent in the composition of the invention are effective over a wide dosage range and are generally administered in a pharmaceutically effective amount. It will be understood, however, that the effective amount of the compound actually administered will be determined in the light of the relevant circumstances, including the condition to be treated, the chosen route of administration, the age, weight, and response of the individual patient, the severity of the patient's symptoms, and the like.

The term "bioactive ingredient" as used herein is intended to mean naturally occurring compounds which in an effective amount provide effective weight reduction treatment of the patient in need thereof. It will be understood that other bioactive ingredients can be used that are capable of inducing a desired response or treating a particular condition.

Formulation/Administration

This composition may be administered in a wide variety of product forms including non-enteric pharmaceutical dosage forms such as compressed and molded tablets, hard gelatin capsules, soft elastic gelatin capsules, and microcapsules that dissolve in the stomach, emulsions, and suspensions, or as part of a beverage or solid food product. The latter may be used as a meal supplement or replacement.

A dose of the invention contains capsaicin in an amount from about 0.1-4.8 mg (10,000-480,000 Scoville heat units), about 101-4,800 mg L-tyrosine, about 12-600 mg supplemental caffeine, about 125-6,000 mg of green tea extract which contains about 31-1,500 mg catechin and about 12-600 mg caffeine, and embodiments which include 50-8000 mg calcium. The dose can be given from 1 to about 10 times daily, preferably from 2 to about 8 times daily, in particular from 2 to about 4 times daily.

The composition according to the present invention may be formulated for administration by any suitable route such as the oral, rectal, nasal, topical (dermal) or parenteral administration route. Thus, the composition may be in the form of tablets, capsules, suspensions, emulsions, solutions, injectables, suppositories, sprays, aerosols and in other suitable form.

Formulations for oral use include tablets which contain the composition in a mixture with non-toxic pharmaceutically acceptable excipients. These excipients may be, for example, inert diluents, such as calcium carbonate, sodium chloride, lactose, calcium phosphate or sodium phosphate; granulating and disintegrating agents, for example, potato starch or alginic acid; binding agents, for example, starch, gelatin or acacia; and lubricating agents, for example, magnesium stearate, stearic acid or talc. Other pharmaceutically acceptable excipients can be colorants, flavoring agents, plasticizers, humectants etc. The tablets may be uncoated or they may be coated by known techniques, optionally to delay disintegration and absorption in the gastrointestinal tract and thereby provide a sustained action over a longer period. For example, a time delay material such as glyceryl monostearate or glyceryl distearate may be employed.

Formulations for oral use may also be presented as chewing tablets or chewing gum, or as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

Powders, dispersible powders or granules suitable for preparation of an aqueous suspension by addition of water are also convenient dosage forms of the present invention. Formulation as a suspension provides the active ingredient in admixture with a dispersing or wetting agent, suspending agent and one or more preservatives. Suitable dispersing or wetting agents are, for example, naturally-occurring phosphatides, as e.g. lecithin, or condensation products of ethylene oxide with e.g. a fatty acid, a long chain aliphatic alcohol or a partial ester derived from fatty acids and a hexitol or a hexitol anhydrides, for example, polyoxyethylene stearate, polyoxyethylene sorbitol monooleate, polyoxyethylene sorbitan monooleate etc. Suitable suspending agents are, for example, sodium carboxymethylcellulose, methylcellulose, sodium alginate etc.

The pharmaceutical formulation may also be administered parenterally (intravenous, intramuscular, subcutaneous or the like) in dosage forms or formulations containing conventional, non-toxic pharmaceutically acceptable carriers and adjuvants. The formulation and preparation of such compositions is well-known to those skilled in the art of pharmaceutical formulation. (Remington's Pharmaceutical Sciences, 1980, 16$^{th}$ Ed. Mack Publishing Company, Eason, USA.)

For parenteral use, the pharmaceutical compositions according to the invention may comprise the compounds in the form of a sterile injection. To prepare such a composition, the compounds are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution and isotonic sodium chloride solution. The aqueous formulation may also contain one or more preservatives, for example, methyl, ethyl or n-propyl p-hydroxybenzoate.

For the rectal application, suitable dosage forms for a composition according to the present invention include suppositories (emulsion or suspension type), and rectal gelatin capsules (solutions or suspensions). In a typical suppository formulation, the thermogenic compounds are combined with an appropriate pharmaceutically acceptable suppository base such as cocoa butter, esterified fatty acids, glycerinated gelatin, and various water-soluble or dispersible bases like polyethylene glycols and polyoxyethylene sorbitan fatty acid esters. Various additives like e.g. enhancers or surfactants may be incorporated.

For the nasal application typical dosage forms for a composition according to the present invention include nasal sprays and aerosols for inhalation. In a typically nasal formulation, the active ingredients are dissolved or dispersed in a suitable vehicle. The pharmaceutically acceptable vehicles and excipients and optionally other pharmaceutically acceptable materials present in the composition such as diluents, enhances, flavoring agents, preservatives etc. are all selected in accordance with conventional pharmaceutical practice in a manner understood by the persons skilled in the art of formulating pharmaceuticals.

The pharmaceutical compositions according to the invention may also be administered topically on the skin for percutaneous absorption in dosage forms or formulations containing conventionally non-toxic pharmaceutically acceptable carriers and excipients including microspheres and liposomes. The formulations include creams, ointments, lotions, liniments, gels, hydrogels, solutions, suspensions, pastes, plasters and other kinds of transdermal drug delivery systems. The pharmaceutically acceptable carriers or excipients may include emulsifying agents, antioxidants, buffering agents, preservatives, humectants, penetration enhancers, chelating agents, gel forming agents, ointment bases, perfumes and skin protective agents.

Examples of emulsifying agents are naturally occurring gums, e.g. gum acacia or gum tragacanth, naturally occurring phosphatides, e.g. soybean lecithin and sorbitan monooleate derivatives. Examples of antioxidants are butylated hydroxy anisole (BHA), ascorbic acid and derivatives thereof, tocopherol and derivatives thereof and cysteine. Examples of preservatives are parabens and benzalkonium chloride. Examples of humectants are glycerin, propylene glycol, sorbitol and urea. Examples of penetration enhancers are propylene glycol, DMSO, triethanoiamine, N,N-dimethylacetamide, N,N-dimethylformamide, 2-pyrrolidone and derivatives thereof, tetrahydrofurfuryl alcohol and Azone™. Examples of chelating agents are sodium EDTA, citric acid and phosporic acid.

Examples of gel forming agents are Carbopol, cellulose derivatives, bentonit, alginates, gelatin and PVP.

Examples of ointment bases are beeswax, paraffin, cetyl palmitate, vegetable oil, sorbitan esters of fatty acids (Span), polyethyleneglycols, and condensation products between sorbitan esters of fatty acids and ethylene oxide, e.g. polyoxyethylene sorbitan monooleate (Tween).

The formulation and preparation of the above-mentioned compositions is well-known to those skilled in the art of pharmaceutical formulation. Specific formulation can be found in "Remington's Pharmaceutical Sciences." (Remington's Pharmaceutical Sciences, 1980, 16$^{th}$ Ed. Mack Publishing Company, Eason, USA)

Preferably, the pharmaceutical composition of the present invention comprises a combination containing the bioactive ingredients: capsaicin and/or capsaicin-like analogs (for example, but not limited to, structural hallmarks being vanillyl core bound to a branched fatty acid thereof, L-tyrosine, supplemental caffeine and/or analogs thereof, green tea extract comprising catechin and caffeine, and embodiments which include calcium. The composition of the invention may be embodied in one or more dosage forms. For example, a single dosage form would contain capsaicin and/or analogs thereof, L-tyrosine, calcium, supplemental caffeine and/or analogs thereof, and green tea extract comprising catechin and caffeine. The ingredients may be distributed among a variety of dosage forms administered so as to deliver an effective amount of the composition of the invention. In the methods of the invention, the ingredients of the composition may be taken in a single dosage form. In other embodiments of the methods, the ingredients comprising an effective amount may be distributed in multiple dosage forms provided that the dosage forms are simultaneously or near-simultaneously administered. In one aspect the present invention relates to a method for reducing the weight of overweight or obesity in individuals, in particular in humans, the method involving administration of an effective amount of the composition of the invention.

In another aspect, the present invention also relates to a method of maintaining weight by subjecting the individual to a diet regimen and the composition and method of the present invention, after a desired amount of weight is lost. The diet regimen may include a low carbohydrate, a low fat and a low energy regimen, e.g. a diet of from 800-2500 kcal/day.

EXAMPLES

The following examples are intended to illustrate specific embodiments of the invention. They are not intended to limit the invention in any manner.

Example 1

Preparation of Composition

Capsules containing the weight loss formulation in accordance with the present invention as a single dosage form having the following composition were prepared as set forth below:

| Ingredient | Amount per capsule |
| --- | --- |
| Capsaicin | 0.1-4.8 mg |
| | (10,000-480,000 Scoville heat units) |
| Green Tea Extract | 125-6000 mg |
| Catechin | 31-1500 mg |
| Caffeine | 12-600 mg |
| Supplemental caffeine | 12-600 mg |

-continued

| Ingredient | Amount per capsule |
| --- | --- |
| L-Tyrosine | 101-4800 mg |
| Elementary Calcium* | 50-8000 mg |

*Calcium supplementation, regardless of the form in which calcium is furnished to the subject, is in the range of 50-8000 mg elementary calcium. The form(s) of calcium in the composition of the invention are selected from calcium bound either in a salt and/or in an organic compound. Calcium salts used in the invention include, but are not restricted to, calcium carbonate, calcium sulfate, dibasic calcium phosphate, calcium sodium magnesium phosphate, monodibasic calciumphosphate, dihydrated dibasic calcium phosphate, calcium sodium phosphate. Forms of calcium bound to organic molecules include, but are not restricted to, calcium lactate, calcium fumarate, calcium malate fumarate, calcium citrate, calcium citrate malate, biolactal calcium, calcium formate, calcium lactogluconate/carbonate.

Capsaicin (*Capsicum annuum* L, cayenne pepper) was obtained from Alpine Health Products, LLC, Orem, Utah. Green tea extract was obtained from Alpine Health Products, LLC, Orem, Utah. Supplemental caffeine was obtained from Alpine Health Products, LLC, Orem, Utah. L-tyrosine was obtained from Alpine Health Products, LLC, Orem, Utah. Elementary calcium was obtained from Alpine Health Products, LLC, Orem, Utah.

Procedure: The dry ingredients were mixed and filled in gelatin capsules using conventional pharmaceutical methods for preparation of capsules.

Example 2

Weight Loss Treatment Protocol: Study 1

Aim

Some bioactive food ingredients exert weak thermogenic effects after acute dosing. The purpose of the present study was to examine if a low dose of a combination of five bioactive food ingredients (capsaicin, catechin, caffeine, tyrosine, and calcium) taken three times a day was able to increase 24-h energy expenditure, and whether a possible effect was maintained after 7-days of chronic intake. An enterocoated preparation was also tested to examine whether local effects of capsaicin in the gastric mucosa had any side effects.

Study Design

The present study was designed as a 3-way crossover, randomized, placebo controlled, double blind study with each treatment period of 7 days separated by a greater than 6 day wash-out. Both supplements (verum treatment) were administered as one tablet containing green tea extract, tyrosine, anhydrous caffeine, and capsaicin. One supplement contained capsaicin in a simple release formulation, the other supplement contained capsaicin in a controlled (enterocoated) release formulation. Both supplements were taken together with one tablet containing biolactacal calcium. The two tablets were taken three times per day. The daily dosage of the bioactive supplement was: green tea extract (750 mg—whereof 188 mg catechins and 75 mg caffeine), tyrosine (609 mg), anhydrous caffeine (76 mg), capsaicin (0.6 mg~120,000 heat units) and biolactacal calcium (1965 mg). The placebo tablets contained an inert vehicle (microcrystalline cellulose) and could not be distinguished from the verum supplements with respect to colour, taste, smell or appearance. Both verum and placebo supplements were taken 30 minutes before breakfast, lunch and dinner. The capsaicin containing tablets were of similar dosage, but differed in release form. The capsaicin compound in the simple release formulation was released in the stomach, whereas the controlled release formulation of the capsaicin component was enterocoated in order to delay uptake until the small intestine. During the study period, the subjects were not allowed to change their dietary and beverage habits, use of spices, level of physical activity, smoking habits, and use of medication.

Subject Selection

Subjects were recruited using advertisement in local newspapers. The inclusion criteria were: men, 18-70y, healthy, overweight to obese (BMI: 25-35 $kg/m^2$), no chronic or frequent use of medication, weight stable (within±3 kg in last 3 mo), non-smoking, non-athletic men. Potential subjects were given written and oral information about the study. Nineteen men (Age: 40.8±13.1 y, BMI: 28.0±2.7 $kg/m^2$) participated in the study. All subjects gave their written consent after having received verbal and written information about the study. The Municipal Ethical Committee of Copenhagen and Frederiksberg approved the study as being in accordance with the Helsinki II Declaration.

Effect Evaluation

On the $7^{th}$ day of each treatment, 24-h energy expenditure (EE), substrate oxidations, spontaneous physical activity (SPA), and heart rate were measured in respiration chambers. Appetite sensations and well-being were measured by visual analogue scales. Spontaneous caloric intake was assessed the following day at an ad libitum intake of a breakfast meal.

Respiratory Measurements

On the seventh and last day of each treatment period, EE and substrate oxidation rates were measured by indirect whole-body calorimetry, based on oxygen uptake, carbon dioxide production and nitrogen excretion from urine in a 14.7-$m^3$ respiratory chamber as previously described in detail (Astrup, A. et al., 1990, Prediction of 24 h energy expenditure and its components from physical characteristics and body composition in normal-weight humans. *Am. J. Clin. Nutr.* 52:777-83). The volume of outgoing air from the chambers was measured by the principle of differential pressure (AVA 500, Hartmann & Braun, Frankfurt, Germany). The concentration of carbon dioxide of the outgoing air was measured by infrared analysis (Urea 3G, Hartmann & Braun) and concentration of oxygen by paramagnetic principle (Mangos 4G, Hartmann & Braun). The chamber temperature was kept approximately on 24° C. during the day (07.30-23.00) and 18° C. during the night (23.00-07.30).

To minimize stress responses, the subjects were instructed to arrive 10 hours prior to the test day and spend the night in the chambers, to let the subjects get accustomed to the milieu. After voiding at 08.00 the following morning, anthropometric measurements were assessed. Body weight was measured to the nearest 0.05 kg on a decimal scale (Lindeltronic 8000, Copenhagen, Denmark) and height to the nearest 0.5 cm. Blood pressure was measured by an automatically inflating cuff (digital blood pressure meter model UA-743, A&D Company Ltd, Tokyo, Japan) and reported as average of two measurements. To detect possible infections, body temperature was assed by digital thermometer (Becton Dickinson, Franklin Lakes, N.J.) and an urine sample, collected at the beginning of the respiratory measurement, was tested using sticks for proteinuria, haematuria, and glucoseuria. Subsequently, urine was collected during the 24 h measurement but separated into day urine (09:00-23:00) and night urine (23:00-09:00). The urine samples were used to adjust the respiratory measurements for nitrogen excretion.

The protocol included standardized respiratory measure of 24-h EE, which was measured at the beginning of the respiratory measurement at 09.00 and continued during the next 24 hours. The basal metabolic rate ($EE_{BMR}$) was measured in the last hour of the chamber stay, 08.00 to 09.00 on the second morning, after 13 h of fasting. Furthermore, EE during sleep was measured from 01.00 to 06.00. Other parameters included in the protocol were 24-h oxidation of macronutrients: carbohydrate ($OX_{cho}$), fat ($OX_{fat}$), and protein ($OX_{prot}$), 24-h respiratory quotient (24-h RQ), and 24-h energy balance (energy balance=energy intake−energy expenditure) in the chamber.

During the chamber stay, the heart rate was registered by a portable ECG devise (Dialogue 2000 type 2070-14 XTNJ, Dania Electronics, Rødovre, Denmark), which was attached to the subjects. SPA was assessed by two microwave radar detectors (Sisor Mini-Radar, Static Input System SA, Lausanne, Switzerland), which continuously emits and receives a signal. The SPA measurements indicate the percentage of time in which the subjects are active to a detectable degree.

The standard 24-h EE protocol contained fixed scheduled physical activity. There was included two sessions of 15 minutes cycling, carried out on an ergometer bicycle (Monark 814E, Monark AB, Varberg, Sweden) with 75 W in work output, as well as two sessions of walking back and forth 25 times in the chamber. Otherwise, only sedentary activities were allowed.

After completion of the respiratory measurement, body weight and blood pressure was assessed. Body composition, fat free mass (FFM) and fat mass (FM), was estimated by bioelectrical impedance analysis using an Animeter (HTS-Engineering Inc, Odense, Denmark) and calculated as previously described. (Lukaski, H. C., et al., 1986, Validation of tetrapolar bioelectrical impedance method to assess human body composition. *J. Appl. Physiol.* 60:1327-32)

Respiration Chamber Diets

The subjects were given three main meals and one snack during the 24-h chamber stay. The diet was identical on each chamber stay. The individual energy intake was a controlled weight-maintenance diet. (Klausen B., et al. 1997, Age and sex effects on energy expenditure, *Am. J. Clin. Nutr.* 65:895-907)

Energy intake (kJ/24 h)=387.8+116.2 FFM (kg)+190.5 SPA (%)+29.2 FM (kg)+41.0 DE (min)+140.4 sex−4.48 age (y), where physical activity (SPA) was estimated to 5.8%, duration of exercise (DE) to 30 min and sex (males) to 1. (Klausen B., et al. 1997, Age and sex effects on energy expenditure, *Am. J. Clin. Nutr.* 65:895-907) The energy content of protein, carbohydrate, and fat were 17%, 56%, and 27%, respectively, calculated by using computerized version of The Danish Nutrient Database, Dankost 2000® version 1.4C (National Food Agency of Denmark, Søborg, Denmark). The subjects were aloud to drink ad libitum water and caffeine-free coffee and tea during the chamber stay.

After completion of respiratory measurements, the subjects were given an ad libitum breakfast 2 h after intake of two tablets (one tablet containing green tea (250 mg), tyrosine (203 mg), anhydrous caffeine (25 mg), capsaicin (0.2 mg) and one tablet biolactacal calcium (655 mg) or two tablets of placebo). The meal was composed of 325 g cheese sandwiches and 150 mL water. The subjects were instructed to eat at a constant pace and to terminate the meal when they felt satiated. Ad libitum energy intake ($EI_{ad}$) was assessed by the consumed amount of the meal.

Questionnaires

To monitor each subject's appetite sensations during the chamber stay, visual analogue scales (VAS) were used. The scales consisted of 10-cm, unmarked, unipolar, horizontal lines with words anchored at each end, expressing the most positive (ie, good or pleasant) or most negative (ie, bad or unpleasant) ratings (Hill, A. J., et al., 1984, Hunger and palatability: tracking ratings of subjective experience before, during and after the consumption of preferred and less preferred food, *Appetite* 5:361-71). The scales contained questions about subjective sensations of hunger, satiety, prospective consumption, fullness, thirst, well-being and desire to eat something sweet, salty, rich in fat, or meat/fish. The subjects were instructed to complete visual analogue scales ½ h before lunch and dinner, 1 h after the beginning of the meals and just after the completion of the respiratory measurement.

At the ad libitum breakfast, identical visual analogue scales were used just before beginning of the meal and after 10, 20 and 30 minutes. To monitor the subjective opinion of organoleptic quality of the meal, visual analogue scales (appearance, smell, taste, after-taste and general palatability) were completed just after termination of the meal.

During the treatment periods, the subjects were supplied with a booklet containing identical questions for each day which were to be completed consecutively. The questionnaires included questions about compliance of treatment, side effects and general well-being.

Statistical Analysis

All results are given in mean and 95% confidence interval (95% CI). The significant level was set at <0.05. Statistical analyses were performed with SAS 8.2 for Windows (SAS Institute, Cary, N.C.). All data was, prior to the statistical analysis, tested for normality by Shapiro-Wilk W test and variance homogeneity. Differences between treatments were tested by analysis of mixed linear models, with or without adjusting for various confounders. Post hoc comparisons were made, with Turkey-Kramer adjustment of significance levels for the pair-wise comparison, using unpaired t-test when the analysis indicated significant treatment effect.

To investigate the influence of various confounders, estimates of the difference between the capsaicin treatments and placebo in 24-h EE were calculated by subtracting placebo from the active treatments ($EE_{treatment}-EE_{placebo}$). Data were analyzed by analysis of mixed linear models. The difference of the active treatment and placebo was significant if zero was not included in the 95% CI. The relationship between 24-h EE and 24-h heart rate (both placebo-subtracted) was tested in a Pearson correlation test.

The ratings of the visual analogue scales were calculated as in area under the curve (AUC) and the difference between treatments was tested by the analysis of mixed linear models adjusted for baseline. Difference between treatments and the prevalence of self-reported side effects was tested by the homogeneity test.

Results

Energy Expenditure

The 7 day treatment had no significant effects on body weight, BMI, fat free mass, or fat mass (Table 1), or on unadjusted 24-h EE, BMR, $EE_{sleep}$, SPA, and energy balance (Table 2). There was no periodic effect on 24-h EE among treatments or any interaction between treatment and the previous treatment (carry-over effect). However, the small group differences in body weight and SPA influenced EE. 24-h EE was adjusted for both covariates, body weight and SPA (Table 3). After adjustment, 24-h EE was increased significantly by 160 kJ/d (95% CI: 15 to 305) by the simple preparation as compared to placebo, whereas the enterocoated preparation had no effect (53 kJ/d, −92 to 198).

On average, the energy balance was slightly negative during the chamber stays among all treatments. The plain formulation produced a significant deficit on 24-h energy balance, 193 kJ/d (49 to 338, P=0.03) compared to placebo. There was no indication of significant difference in unadjusted or adjusted BMR, $EE_{sleep}$, or 24-h respiratory quotient (Table 2).

The relationship between the placebo-subtracted 24-h EE of both active treatments was found to positively correlate with the placebo-subtracted heart rate (plain formulation, r=0.53, p=0.02; enterocoated formulation, r=0.47, p=0.04) (FIG. 1).

Substrate Oxidation

There was no treatment effect on 24-h protein, carbohydrate or fat oxidation, and this was not altered by adjustment for energy balance and body weight (Table 4).

Spontaneous Physical Activity, Heart Rate and Blood Pressure

Total unadjusted 24-h SPA was similar with both treatments and with placebo. The same applied for heart rate, and diastolic and systolic blood pressure (Table 2).

Appetite Sensations and Ad Libitum Intake

Figure 2:
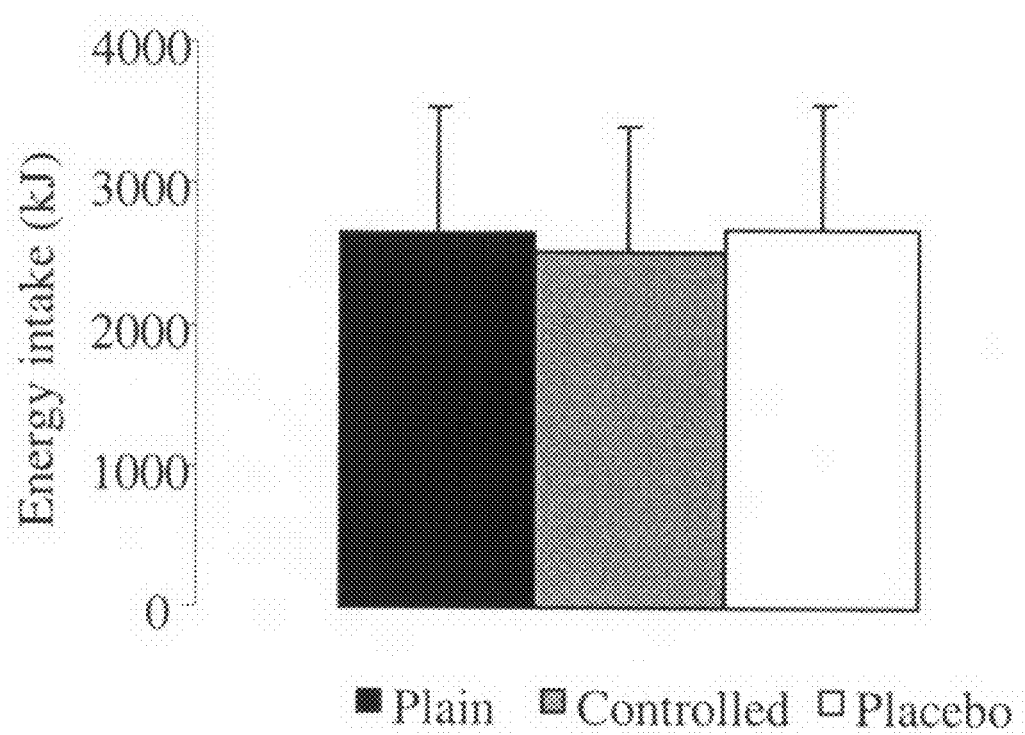
FIG. 2: Ad libitum energy intake (kJ) of 19 overweight men. The ad libitum meal was served as breakfast after completion of the chamber stay and 2 hours after tablet supplementation. Data are presented as mean±SD and were analyzed by mixed linear models with the dependent variable adjusted for period. No significant difference was found between treatments.

Treatment period exerted a strong confounding effect (p=0.0005) on energy intake at the ad libitum test meals. There was no significant effects of bioactive supplements versus placebo. However, energy intake decreased by 6% following the enterocoated formulation as compared to placebo (−180 kJ (−458:98), adjusted −154 kJ (−385:76) (FIG. 2). The energy intake was similar on the simple formulation and on placebo (−78 kJ (−356:201), adjusted −27 kJ (−282:228)). There was no significant effect of either meal sequence or time on energy intake.

At the ad libitum meal the visual analogue scale ratings of the appetite sensations showed no significant difference between the supplements. Subjects rated the organoleptic quality of the meal as mediocre, and there was no significant difference between supplements.

Side Effects

In general, the frequency of self-reported side effects was similar among treatments. However, the placebo supplement gave rise to a higher frequency of headaches than did the bioactive supplements (Table 5). Borborygmia and flatulence were reported by 16 and 11% of the subjects on the simple and enterocoated versions, respectively.

Summary

After adjustment for changes in body weight, SPA, and energy intake, 24-h EE was increased by 160 kJ/d (95% CI: 15 to 305) by the simple preparation as compared to placebo, whereas the enterocoated preparation had no effect (31 kJ/d, −73 to 135; simple vs. enterocoated versions, P=0.01). The plain preparation produced a deficit on 24-h energy balance of 193 kJ/d (49 to 338, P=0.03). The enterocoated supplements insignificantly decreased ad libitum food intake by 6% whereas the simple formulation had no effect compared to placebo. None of the bioactive supplement had no detectable effect on substrate oxidations, SPA, heart rate or general well-being.

Subjects rated the organoleptic quality of the meal as mediocre, and there was no significant difference between supplements.

The simple supplement containing bioactive food ingredients was able to increase daily EE by 160 kJ/day (95% CI: 15-305) compared to the placebo treatment without raising heart rate or producing other adverse effects. The inability of the enterocoated supplement to increase EE suggests that a local action of capsaicin in the gastric mucosa is a prerequisite for exerting the thermogenic effect. The weight reduction effect brought about by a combination of an effective amount of bioactive ingredients of the composition: capsaicin, tyrosine, supplemental caffeine, calcium, and green tea extract comprising catechin and caffeine. This effect produced a marked suppression of hunger, stimulated energy expenditure and fat oxidation, thereby producing weight loss in overweight and obese subjects. Additionally, the significant thermogenic effect of the composition of the invention in the present study was still present after 7 days of chronic treatment.

Example 3

Weight Loss Treatment Protocol: Study 2

Aim

The aim of this study was to investigate whether the thermogenic effect of the compound of the invention (Example 1) was maintained beyond the 7 days tested in study one (Example 2), and whether the negative energy balance translated into a loss of body fat over 8 weeks.

Subject Selection

The subjects were selected as described in Example 2. Ninety-three healthy Danish overweight to obese (mean BMI: 31.3±2.6 kg/m², age: 46.2±11.8 y, 23 males) were recruited for participation.

Experimental Protocol

The study period lasted 12 weeks. The intervention design was an 8-week randomized 3-arm parallel, placebo-controlled and double-blind intervention. Prior to the randomized intervention a weight loss was initiated by 4 week treatment with a 3.4 MJ/d low caloric diet (LCD) (Speasy®, Dansk Droge, Ishøj, Denmark), consisting of 6 meals of 37 g formula suspended in 250 ml water. The diet provided 75 g protein (7 g caseinat, 68 g soy protein), 96 g carbohydrate (16 g maltodextrin, 80 g fructose), 15 g oat fibre, and 12 g unsaturated fat per day. Of the 93 subjects enrolled in the LCD phase, eighty subjects fulfilled the pre-defined requirement to loose more than 4% of their initial body weight after the 4 weeks LCD treatment were randomized to the weight maintenance phase of the study. One subject did not meet the above criteria and was excluded from the study. Furthermore, 13 subjects dropped out of the LCD phase due to lack of ability to follow the study protocol (12) and illness (1).

Eighty subjects (BMI: 31.2±2.5 kg/m², age: 47.6±11.0 y, 18 males) were randomized into 3 groups i.e. placebo (n=23, 4 men), simple release bioactive group (n=29, 8 men) and enterocoated release bioactive group (n=28, 6 men). The simple and enterocoated release bioactive supplements were identical apart from the release form. The bioactive supplements were administered as 9 tablets in total per day containing green tea extract (1500 mg—whereas 375 mg catechins and 150 mg caffeine), tyrosine (1200 mg), anhydrous caffeine (150 mg), calcium carbonate (3890 mg whereof 2000 mg elementary calcium) simple or controlled (enterocoated) release form of capsaicin (1.2 mg~240,000 Scoville heat units). The capsaicin containing tablets were of similar dosage, but differed in release form. The capsaicin compound in the simple release formulation was released in the stomach whereas the controlled release formulation the capsaicin component was enterocoated in order to delay uptake until the small intestine. The placebo tablets contained 50/50 microcrystalline cellulose and maltodextrin and could not be distinguished from the bioactive supplements with respect to the 9 tablets per day, color, taste, smell or appearance. Active or placebo supplements were taken as 3 tablets 30 minutes before breakfast, lunch and dinner. The study compounds were distributed to the subjects in tablet bottles. As a compliance indicator, the subjects returned the tablet bottle every fortnight and the remaining tablets were counted.

During the intervention all subjects received dietary instruction to a slightly hypocaloric diet providing −1250 kJ/d using an isoenergetic educational system. The dietary advice was reinforced by dietetic consultations every fortnight. The subjects were not allowed to change their dietary and beverage habits (including intake of coffee and tea), use of spices, level of physical activity, smoking habits, and use of medication throughout the study period.

Furthermore, the subjects were supplied with a booklet containing identical questions for each day to be completed consecutively during the supplementation period. The questionnaires included questions about compliance to treatment (daily accurate time for intake and number of tablets taken), side effects and general well-being.

Five participants (4 male) dropped out of the phase 2 part of the study due to lack of ability to follow the study protocol (n=2 enterocoated), illness (n=1 placebo) and chronic nausea/vertigo (n=1 placebo (female), n=1 simple).

Methods

Assessment of anthropometric measures was preformed as described in Example 2. All participants underwent assessments of resting metabolic rate (RMR) and respiratory quotient (RQ) by indirect calorimetry using a ventilated hood system. RMR was calculated using a formula assuming a fixed protein catabolism as the error of calculating RMR by omitting the exact correction from urinary nitrogen is negligible and too weak to estimate during a short time period. The precision of the ventilated hood system was validated by an alcohol burning test on weekly basis; CV % was 1.5.

The respiratory measurements were of 5-h duration i.e. from 8 a.m. to 1 p.m. and were conducted at initiation and completion of the intervention (first and last day of intervention). Before each 5-h respiratory measurement the participants rested in a supine position for 30 minutes. Between 8 and 9 a.m. two baseline measurements (2×25 minutes) were assessed. Afterwards the participants ingested ⅓ of the daily dose of medication whereupon 25-minutes respiratory measurements were repeated 8 times during the next 4 hours. The participants were instructed to fast for 10-h before the measurement. The subjects abstained from other than habitual medication and alcohol and hard physical activity for 24-h before the two respiratory measurements. To limit diurnal variation and inter- and intra subject variations, all measurements were be carried out according to an identical time schedule and at the same time of the day.

Urine and Fecal Samples

The subjects collected all feces for duration of three consecutive days within one week prior to each respiratory measurement. All feces were collected in preweighed containers. The fecal samples were weighed and frozen at −20° C. Before analysis the samples were freeze-dried and homogenized, and samples from the same collection period were pooled. Fecal energy was obtained using a bomb calorimeter (Ikacalorimeter system C4000 Heitersheim, Germany). $CV_{intra}$ and $CV_{inter}$ were 0.1% and 0.2%, respectively. Before fat content was measured the samples were acid hydrolyzed with 3 N HCl. Total fat content was measured by a method modified after Bligh & Dyer. (Bligh, E. G., & Dyer, W. J., 1959, A rapid method of total lipid extraction and purification. *Can. J. Biochem. Physiol.* 37: 911-7).

In addition, all subject collected 24-h urine during each feces collection periods. As a biomarker of complete urine samples, 3 tablets with a total of 240 mg 4-aminobenzoic acid (PABA) were taken at meal times. The volume and density of each 24-h urine collection were determined, and 4 samples were frozen at −20° C. until further analysis. Urine samples were analyzed for aromatic amines (PABA) by colorimetric method using a spectrophotometer (Stasar; Gilford Instruments Laboratories Inc, Oberlin, Ohio) with $CV_{intra}$ and $CV_{inter}$ 2.3% and 2.1%, respectively. Urine samples with a PABA recovery 85% were considered incomplete urine collections. Nitrogen content was measured using the Dumas method with a nitrogen analyser (NA1500, Carlo Erba Strumentazione, Milano, Italy). $CV_{intra}$ and $CV_{inter}$ were 1.1% and 1.6%, respectively. Urinary calcium concentration was measured using atomic absorption on a Spectra AA-200 (Varian, Victoria, Austrailia). $CV_{intra}$ was 2.1% and $CV_{inter}$ was 2.9%. Urinary content of catechols was determined using high-performance liquid chromatography (HPLC) methods.

Stastistical Analysis

First the effect of the bioactive compound was assessed by analyzing the two groups together as one group versus placebo. Subsequently, the two bio-active groups were compared. As no significant difference was found between the two bioactive groups regarding fat loss, and of the thermogenic effect of the supplement at first and last exposure of treatment and therefore no indication of any effect on thermogenesis and fat loss of the release form.

All results are given in mean and standard deviation (SD). The significant level was set at <0.05. Statistical analyses were performed with SAS 8.2 (SAS Institute, Cary, N.C.). All data was analysed as intention-to-treat and the last observation was carried forward. Prior to the statistical analysis all data was tested for normality by Shapiro-Wilk W test and variance homogeneity and data-transformed if necessary. Differences in between supplements were tested by analysis of variance (general linear models (GLM)), with or without adjusting for various confounders. Post hoc comparisons were made, with Turkey-Kramer adjustment of significance levels for the pair wise comparison, using unpaired t-test when the analysis indicated significant treatment effect.

Respiratory measurements (4-h RMR and RQ) were tested by mixed linear models procedure as repeated measurement adjusted for baseline level. Furthermore, after subtraction of the baseline level ratings of RMR and RQ were calculated as an area under the curve (AUC). Difference between initiation and completion of the intervention was tested by ANCOVA adjusted for baseline both within and between supplements.

The relationship between changes in 4-h RMR (AUC) and anthropometric and hemodynamic measures during the intervention was tested in a Pearson correlation test. Difference between treatments in the prevalence of self-reported adverse events was tested by homogeneity test.

Results

Body Weight and Composition

At baseline there was no difference between the groups that were later randomized into the 3 weight maintenance groups with respect to BMI, waist circumference, body weight and composition. BMI, waist circumference, body weight and composition were reduced significantly during the LCD period compared to the baseline levels. However, the changes were not significantly different between the groups (Table 6).

At initiation of the randomized supplementation period, baseline BMI, waist circumference, body weight and composition were not significantly different between groups (Table 7). During the supplementation period body weight, BMI and waist circumference were reduced significantly reduced in both groups. In the placebo group body weight decreased by 1.1±2.4 (n=23, P=0.04) and in the active group by 1.3±2.2 kg (n=57, P<0.0001). This weight loss, however, was not statistically significant different from the placebo group (Table 6).

Fat mass was reduced by 1.8±2.1 kg in the active group (P<0.01), versus 0.8±2.4 kg in the placebo (P=NS) (active vs. placebo P<0.10). Because the size of the weight loss in the LCD phase as well as the fat mass size are known determinants of the weight loss during the randomized part of the trial, we analyzed the changes in fat mass in the randomized phase with initial body fat mass (P<0.04) and weight changes during the LCD period (P<0.001) as covariates. In this analysis the fat loss in the active group of 1.8±2.1 kg was significantly greater than that the 0.8±2.4 kg in the placebo group, the difference being 0.9 (95% CI 0.5: 1.3) kg fat (P<0.05). The reduction of percentage of total body fat supported these findings. The percentage of body fat mass was significantly reduced during the intervention in the active group by 1.6±2.0% (P<0.0001). The placebo group was insignificantly reduced by 0.7±2.4%. When comparing the groups with respect to body fat (%) loss there was a difference: −1.6±2.0% (P<0.001) in the bioactive versus being 0.9% (95% CI 0.6: 1.3, P=0.075). Adjusting for the percentage body fat mass (P<0.04) at initiation of the supplementation and weight changes during the LCD period (P<0.001) the change of percentage of total body fat was significantly different between groups, active group: −1.7±2.1% vs. placebo: −0.6±2.4% (P=0.03).

Compliance

Compliance with treatment of the placebo and active group was 95.1±6.6% and 94.7±7.8%, respectively. No significant difference was found between the groups.

Resting Metabolic Rate and Respiratory Exchange Ratio

After adjustment for baseline RMR the repeated measurement of RMR on the first day of intervention (FIG. 3A) showed that the bioactive supplement caused significant increase in resting metabolic rate as compared to placebo by 87.3 (50.9:123.7) kJ/4 h, p=0.005 (FIG. 3A) After 8 weeks of sub-chronic supplementation, the effect of the bioactive supplement on RMR was maintained as the bioactive supplement caused a significant increase in resting metabolic rate as compared to placebo by 85.5 (47.6:123.4) kJ/4 h, p=0.03, (FIG. 3B). Furthermore, no significant change in 4-h measurements of RMR or baseline values was found between the first and last exposure of treatment in any of the groups. The bioactive supplement was not different between the first exposure and after 8-week treatment, which suggests that the thermogenic effect was not attenuated during chronic treatment, since the bioactive supplement caused a 2.4% increase in 4-h RMR (99.7±19.2 kJ/4 h, p<0.001) when adjusted for the interaction between time and treatment.

Baseline values and 4-h repeated measurements of RER were similar in both treatments at initiation and completion of the intervention period. Furthermore, the changes in 4-h RER and baseline values between start and completion of the intervention showed no significant difference between supplements.

Hemodynamic Measures

Figure 4:
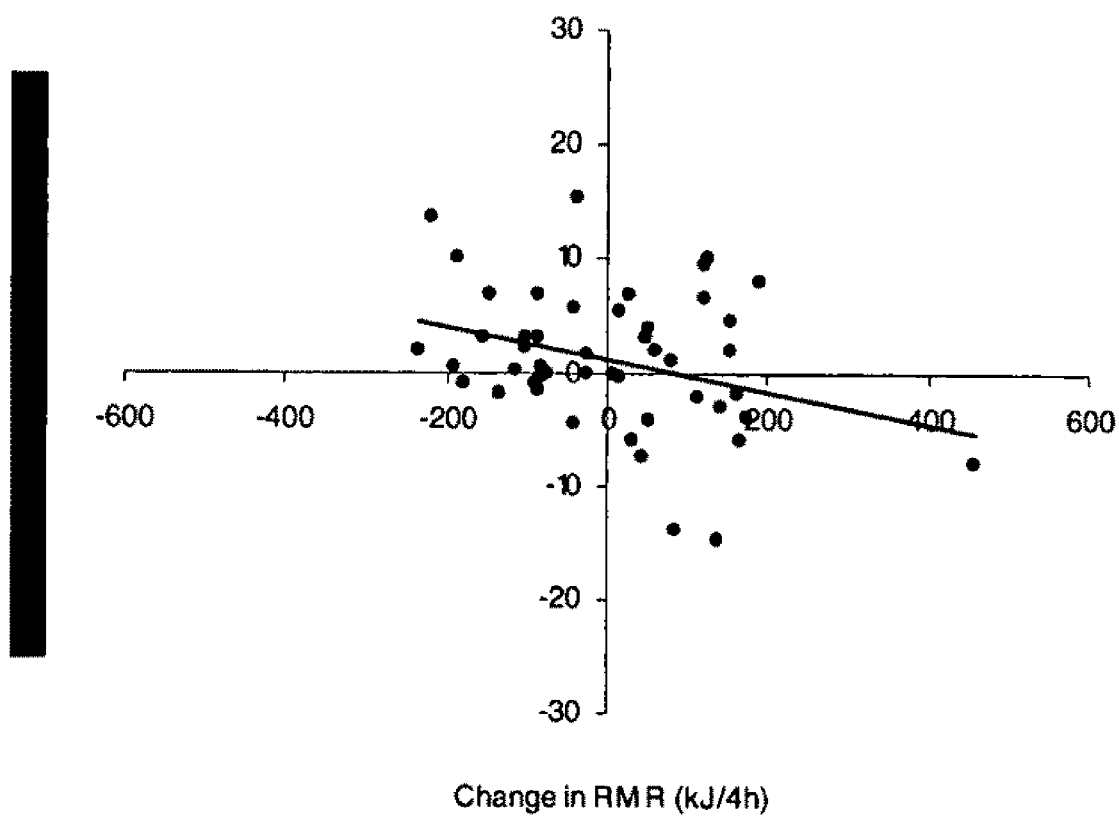
FIG. 4: Relationship between changes in 4-h RMR and diastolic blood pressure in the active group, n=48, 11 males. Data analysed by Pearson correlation (r=0.3, p=0.03).

In both groups, heart rate, systolic and diastolic blood pressure was reduced significantly during the LCD period compared to the baseline levels (Table 6). During the weight maintenance phase heart rate, systolic or diastolic blood pressures were not significantly different from the changes in the placebo group. However, heart rate was increased significantly by 5.6% (3.2±7.6 bpm, P=0.003) in the active group, but this change was not different from the increase in the placebo group of 2.5±6.6 bpm. Although changes in RMR, body composition and homodynamic measures were observed during the intervention, no relationship was found between changes in RMR and body weight and composition. However, a significant correlation was found between change in RMR and diastolic blood pressure (r=−0.3, p=0.03) between the groups (FIG. 4).

Fecal Excretion of Energy and Fat

The active group excreted 14% more energy compared to placebo (adjusted for baseline fecal energy excretion P=0.5) (Table 8). No significant difference was found between groups regarding changes between LCD and intervention. Change in excretion of fecal fat from the LCD period and the intervention was not significant different between groups (Table 8).

Urinary Excretion of Nitrogen, Calcium and Catecholamines

Nitrogen excretion was similar between groups during the LCD and the intervention periods (Table 8). The calcium excretion level was significantly higher in the intervention group compared to placebo (adjusted for baseline: 38±20 (mean±SE), P=0.03). The norepinephrine levels were higher in the active groups during both periods and the adrenalin levels lower compared to placebo (Table 8). When comparing the changes in norepinephrine and epinephrine between the to period no significant difference was found between groups, 7.1 nmol/day (95% CI: −16.6; 30.9), P=0.8, and 1.1 nmol/day (95% CI: −3.8; 6.0), P=0.8, respectively.

Adverse Events (AE)

The two groups were homogeneous with respect to the frequency of specific types of self-reported AE and total sum of self-reported AEs during the 8-week supplementation (P=NS) (Table 9). However, the placebo supplement gave rise to a higher frequency of headaches than verum (Table 9). No difference was found between groups in regard to gastrointestinal problems (P=NS).

Prevention or Inhibition of Weight Regain After Desired Weight Loss

The results show that the thermogenic effects of the composition of the invention administered after a desired weight loss apparently inhibited weight re-gain. Accordingly, a method of the invention includes preventing or inhibiting weight re-gain after desired weight loss by administering the composition of the invention in protocols as described above.

Specifically, the study which supports this utility of the invention is part of the above-reported findings in which:

Design: 80 overweight-obese subjects (BMI: 31.2±2.5 kg/m2, mean±SD) underwent an initial 4-week hypocaloric meal replacement diet (3.4 MJ/d). Those who lost >4% received instruction to a hypocaloric diet (−1.3 MJ/d), and were randomized to receive either placebo (n=23) or bioactive supplement (n=57) in a double-blind, 8-weeks intervention. The thermogenic effect of the compound was tested at the first and last day of intervention, and body weight and composition, blood pressure and heart rate were assessed.

Results: The weight reduction during the weight loss induction phase was 6.8±1.9 kg. At the first exposure the thermogenic effect of the bioactive supplement exceeded that of placebo by 87.3 kJ/4 h (95% CI: 50.9; 123.7, P=0.005), and after 8 weeks this effect was sustained (85.5 kJ/4 h (47.6; 123.4), P=0.03). Body fat mass decreased more in the supplement group by 0.9 kg (0.5; 1.3) compared with placebo (P<0.05). The bioactive supplement had no effect on fecal fat excretion, blood pressure or heart rate.

Example 4

Weight Loss Treatment Protocol: Study 3

Following the protocols of Examples 1, 2, and 3, a study is conducted using the composition below. The results show that the composition of the invention results in weight loss and inhibition of weight re-gain, brought about by a combination of an effective amount of bioactive ingredients of the composition: capsaicin, tyrosine, supplemental caffeine, and green tea extract comprising catechin and caffeine.

| Ingredient | Amount per capsule |
|---|---|
| Capsaicin | 0.1-4.8 mg |
|  | (10,000-480,000 Scoville heat units) |
| Green Tea Extract | 125-6000 mg |
| Catechin | 31-1500 mg |
| Caffeine | 12-600 mg |
| Supplemental caffeine | 12-600 mg |
| L-Tyrosine | 101-4800 mg |

While the invention has been described by reference to specific embodiments, this is for illustrative purposes only. Various modifications to the above invention will become apparent to those skilled in the art, all of which are intended to fall within the spirit and scope of the present invention. All patents and publications referred to herein are hereby incorporated by reference.

TABLE 1

Physical characteristics of the 19 subjects measured after the first 24-h respiratory chamber stay

|  | Plain treatment | Controlled treatment | Placebo |
|---|---|---|---|
| Body weight (kg) | 90.2 (86.1:94.6) | 90.1 (86.1:94.5) | 89.9 (86.2:94.3) |
| BMI (kg/m$^2$) | 27.7 (26.6:28.8) | 27.6 (26.6:28.8) | 27.6 (26.6:28.7) |
| Fat-free mass (kg) | 65.4 (63.1:68.0) | 65.6 (63.3:68.1) | 65.5 (63.3:68.0) |
| Fat mass (kg) | 24.7 (22.4:27.2) | 24.4 (22.1:26.9) | 24.3 (22.0:26.8) |

Mean (95% CI), n = 57 observations. Data analyzed in mixed linear models

TABLE 2

Energy expenditure (EE), energy balance, physical activity level (SPA), systolic and diastolic blood pressure (SBP and DBP, respectively) and heart rate measured for 24-h in a respiratory chamber.

|  | Plain treatment | Controlled treatment | Placebo |
|---|---|---|---|
| 24-h EE (MJ/d)[1] | 11.1 (10.7:11.5) | 10.9 (10.5:11.5) | 10.9 (10.4:11.4) |
| 24-h EE$_{adj}$[2] (MJ/d) | 11.1 (10.8:11.3)[a] | 11.0 (10.7:11.2) | 10.9 (10.7:11.2) |
| BMR-EE (kJ/h)[1] | 386 (363:407) | 379 (354:398) | 378 (355:403) |
| BMR-EE$_{adj}$[2] (kJ/h) | 386 (374:397) | 384 (373:395) | 383 (372:395) |
| Sleep-EE (kJ/h) | 342 (325:359) | 337 (320:354) | 342 (325:358) |
| Sleep-EE$_{adj}$[2] (kJ/h)[1] | 340 (331:348) | 337 (329:346) | 338 (330:347) |
| Energy intake (MJ/day) | 10.2 (9.8:10.5) | 10.2 (9.8:10.5) | 10.2 (9.8:10.5) |
| 24-h energy balance (kJ/d) | −959 (−1336:−582) | −790 (−1167:−413) | −758 (−1135:−381) |
| 24-h energy balance$_{adj}$[3] (kJ/d) | −947 (−1308:−587)[b] | −806 (−1167:−446) | −754 (−1114:−393) |
| SBP (mmHg) | 125 (119:131) | 119 (113:126) | 121 (115:127) |
| DBP (mmHg) | 75 (70:80) | 72 (67:77) | 73 (68:78) |
| Heart rate (bpm)[1] | 67.0 (63.8:70.4) | 65.6 (61.7:69.2) | 65.9 (63.1:69.2) |
| Heart rate$_{adj}$[2] (bpm) | 67.4 (63.8:70.9) | 66.0 (62.4:69.6) | 66.3 (62.7:69.9) |
| Respiratory quotient | 0.84 (0.83:0.85) | 0.84 (0.83:0.85) | 0.84 (0.82:0.85) |
| SPA (%) | 8.4 (7.8:9.0) | 8.28 (7.7:8.9) | 8.4 (7.8:9.0) |

Mean (95% CI), n = 57 observations. Nonadjusted and adjusted variables analyzed in mixed linear models.
Pairwise comparisons between supplements were adjusted with Turkey-Kramer test.
[1]log transformed
[2]Adjusted for weight, SPA
[3]Adjusted for weight and 24-h SPA
[a]Tendency for significant difference between the plain treatment and placebo, P = 0.06
[b]Significant difference between the plain treatment and placebo, P < 0.05

TABLE 3

Placebo-subtracted 24-h energy expenditure before and after adjustment for various confounders.

| Adjustment | Significance of covariable(s) | Plain vs placebo | Controlled vs. placebo | Difference between supplements |
|---|---|---|---|---|
| No adjustment |  | 181 (−19:374) | 32 (−168:232) | P = 0.07 |
| BW | p = 0.001 | 168 (−1:336) | 45 (−123:214) | P = 0.08 |
| 24-h SPA | p = 0.001 | 168 (4:331) | 45 (−118:208) | P = 0.1 |
| BW/24-h SPA | p = 0.03/0.04 | 160 (15:305) | 53 (−92:198) | P = 0.09 |

BW: placebo-subtracted bodyweight (kg); 24-h SPA: placebo-subtracted 24-h spontaneous physical activity (%).
Mean (95% CI), n = 38 observations. Data were analyzed in mixed linear models

TABLE 4

Substrate oxidation measured during the 24-h respiratory chamber stay.

|  | Plain treatment | Controlled treatment | Placebo |
|---|---|---|---|
| Protein oxidation$_{adj}$ (%) | 15.8 (14.9:16.7) | 15.6 (14.7:16.5) | 15.8 (15.0:16.7) |
| Carbohydrate oxidation$_{adj}$ (%) | 38.6 (34.7:42.6) | 39.6 (35.6:43.5) | 38.2 (34.3:42.2) |
| Fat oxidation$_{adj}$ (%) | 45.6 (41.6:49.5) | 44.8 (40.9:48.7) | 45.9 (42.0:49.8) |

Mean (95% CI), n = 57 observations

Variables were adjusted for energy balance and weight and analyzed by mixed linear models with the dependent variable adjusted for different confounders. Subjects were set as random variable and subjects and treatment as class variables.

TABLE 5

Number of subjects reporting side effects during 7-day treatment with the plain version of the supplement, the controlled, and the placebo.

| Side effects | Plain treatment | Controlled treatment | Placebo |
|---|---|---|---|
| Stomach pain | 2 | 1 | 2 |
| Watery faeces | 2 | 1 | 4 |
| Blood in faeces | 1 | | |
| Increased defecation frequency | 1 | 2 | 1 |
| Constipation/inspissated faeces | 2 | 1 | 1 |
| Painful urination/defecation | 2 | 1 | 1 |
| Borborygmia/flatus | 3 | 2 | |
| Headache | 1 | 2 | 5 |
| Decreased appetite | | 1 | |
| Increased appetite | 1 | | 1 |
| Heartburn | 1 | 2 | 1 |
| Increased thirst | | 3 | 1 |
| Nausea/vertigo | 1 | 1 | 1 |
| Increased sweating | | 1 | 2 |
| Total[a] | 17 | 18 | 20 |

[a]Homogeneity test was used when testing the difference between supplements in the prevalence of total self-reported side effects (P = NS).

TABLE 6

Mean decreases (mean ± S.D.) for efficacy outcome by group

|  | Placebo group (n = 23, 4 males) | Intervention group (n = 57, 14 males) | P-value |
|---|---|---|---|
| Weight loss (kg) | | | |
| LCD | −6.6 ± 1.9 | −6.8 ± 2.0 | 0.66 |
| Intervention | −1.1 ± 2.4 | −1.3 ± 2.2 | 0.69 |
| BMI (kg/m²) | | | |
| LCD | −2.4 ± 0.6 | −2.3 ± 0.6 | 0.66 |
| Intervention | −0.4 ± 0.9 | −0.5 ± 0.8 | 0.75 |
| Fat mass (kg) | | | |
| LCD | −4.1 ± 1.9 | −4.1 ± 2.2 | 0.95 |
| Intervention | −0.8 ± 2.4 | −1.8 ± 2.1 | 0.09 |
| Fat free mass (kg) | | | |
| LCD | −2.5 ± 2.3 | −2.7 ± 2.0 | 0.74 |
| Intervention | −0.1 ± 2.2 | 0.5 ± 1.7 | 0.21 |
| Percentage fat | | | |
| LCD | −2.0 ± 2.3 | −2.0 ± 2.1 | 0.90 |
| Intervention | −0.7 ± 2.4 | −1.6 ± 2.0 | 0.08 |
| Waist circumference (cm) | | | |
| LCD | −5.7 ± 2.4 | −6.3 ± 3.4 | 0.43 |
| Intervention | −3.0 ± 3.0 | −3.0 ± 3.9 | 0.98 |
| Systolic blood pressure (mmHg) | | | |
| LCD | −10.5 ± 13.3 | −7.0 ± 14.4 | 0.33 |
| Intervention | 0.4 ± 10.2 | 0.7 ± 9.8 | 0.90 |
| Diastolic blood pressure (mmHg) | | | |
| LCD | −5.7 ± 6.6 | −3.9 ± 6.8 | 0.28 |
| Intervention | 1.4 ± 4.1 | 1.1 ± 5.8 | 0.83 |
| Heart rate (bpm) | | | |
| LCD | −8.0 ± 7.7 | −8.5 ± 6.9 | 0.77 |
| Intervention | 2.5 ± 6.6 | 3.2 ± 7.6 | 0.72 |

TABLE 7

Physical characteristics (mean ± S.D.) at baseline of the 8-week intervention for the placebo and intervention groups[a].

|  | Placebo group (n = 23) | Intervention group (n = 57) |
|---|---|---|
| Females/males | 19/4 | 43/14 |
| Age, y | 51.0 ± 10.5 | 46.2 ± 10.9 |
| Body weight, kg | 80.8 ± 8.2 | 84.2 ± 10.9 |
| BMI, kg/m² | 29.2 ± 2.4 | 28.8 ± 2.6 |
| Fat mass, kg | 29.7 ± 7.3 | 28.7 ± 7.2 |
| Fat free mass, kg | 51.2 ± 8.1 | 55.5 ± 10.8 |
| Total body fat mass, % | 36.7 ± 7.9 | 34.3 ± 7.6 |
| Waist circumference, cm | 101.6 ± 5.9 | 100.9 ± 8.2 |
| Systolic blood pressure, mmHg | 114 ± 10 | 114.7 ± 11.4 |
| Diastolic blood pressure, mmHg | 70.4 ± 5.7 | 71.3 ± 8.2 |
| Heart beat, bpm | 59.3 ± 8.3 | 56.9 ± 7.8 |

[a]No significant difference in baseline values between groups (p < 0.05) at initiation of intervention.

TABLE 8

Excretion of faecal energy and lipids and excretion of urine calcium, nitrogen and catecholamines (mean ± S.D) during the LCD and intervention period in the placebo and intervention group.

|  | Placebo group (n = 21, males) | Intervention group (n = 54, males) | P-value |
|---|---|---|---|
| Fecal energy (kJ/g dry weight) | | | |
| LCD | 16.9 ± 1.4 | 17.1 ± 1.7 | P = 0.6 |
| Intervention[1] | 20.5 ± 1.9 | 19.1 ± 2.0 | P = 0.004 |
| Fecal energy (kJ/day) | | | |
| LCD | 431.3 ± 158.1 | 601.1 ± 384.0 | P = 0.07 |
| Intervention[1] | 841.5 ± 426.4 | 903.2 ± 464.1 | P = 0.5 |
| Fecal fat (g/day) | | | |
| LCD | 4.1 ± 1.9 | 5.0 ± 2.6 | P = 0.2 |
| Intervention[1] | 8.3 ± 5.3 | 8.7 ± 4.3 | P = 0.7 |
| U-nitrogen (mg/day) | | | |
| LCD | 10.1 ± 2.1 | 10.4 ± 2.6 | P = 0.6 |
| Intervention[1] | 12.5 ± 3.2 | 12.7 ± 3.4 | P = 0.3 |
| U-calcium (mg/day) | | | |
| LCD | 106.6 ± 50.0 | 114.1 ± 59.4 | P = 0.6 |
| Intervention[1] | 174.1 ± 75.5 | 219.6 ± 104.4 | P = 0.03 |
| U-norepinephrine (nmol/day) | | | |

TABLE 8-continued

Excretion of faecal energy and lipids and excretion of urine calcium, nitrogen and catecholamines (mean ± S.D) during the LCD and intervention period in the placebo and intervention group.

|  | Placebo group (n = 21, males) | Intervention group (n = 54, males) | P-value |
|---|---|---|---|
| LCD | 259.4 ± 83.0 | 283.5 ± 117.1 | P = 0.4 |
| Intervention[1] | 323.1 ± 93.7 | 356.1 ± 158.8 | P = 0.7 |
| U-epinephrine (nmol/day) | | | |
| LCD | 40.0 ± 22.2 | 34.0 ± 17.6 | P = 0.2 |
| Intervention[1] | 42.1 ± 18.5 | 36.0 ± 18.5 | P = 0.5 |

[1]Adjusted for LCD levels

TABLE 9

Proportion of subjects reporting adverse events (AE) during 8-week treatment with the simple version of the supplement, the enterocoated supplement, and the placebo.

|  | Placebo n = 21 | Intervention group n = 55 | Total n = 75 |
|---|---|---|---|
| Gastro-intestinal problems | 47.6 | 32.7 | 37.3 |
| Gall bladder stones | 4.8 | 3.6 | 4.0 |
| Headache | 52.4 | 32.7 | 38.7 |
| Vertigo | 4.8 | 3.6 | 4.0 |
| Heartbeat |  | 1.8 | 1.3 |
| Shivering |  | 1.8 | 1.3 |
| Increased sweating |  | 1.8 | 1.3 |
| Nose bleeding |  | 1.8 | 1.3 |
| Insomnia |  | 1.8 | 1.3 |
| Cold/flu | 19.0 | 18.2 | 18.7 |
| Swollen legs |  | 1.3 | 1.3 |
| Knee pain |  | 1.9 | 4.0 | 4.0 |
| Total | 138.1 | 103.7 | 114.7 |

<sup>a</sup>Homogeneity test was used when testing the difference between supplements in the prevalence of self-reported AE. The two groups were homogeneous with respect to the prevalence of specific self-reported AE and total sum of self-reported AEs (P = NS).

What is claimed is:

1. A composition for increasing thermogenesis or reducing appetite consisting essentially of:
   0.1 to 4.8 mg capsaicin comprising 10,000 to 48,000;
   101 to 4800 mg L-tyrosine;
   12 to 600 mg supplemental caffeine; and
   125 to 6000 mg of green tea extract, wherein the green tea extract contains 12 to 600 mg by weight of caffeine and 31 to 1500 mg catechin.

2. A composition for increasing thermogenesis or reducing appetite consisting essentially of:
   0.1 to 4.8 mg capsaicin comprising 10,000 to 48,000 Scoville heat units;
   101 to 4800 mg L-tyrosine;
   12 to 600 mg supplemental caffeine;
   125 to 6000 mg of green tea extract, wherein the green tea extract contains 12 to 600 mg by weight of caffeine and 31 to 1500 mg catechin; and 50 to 8000 mg elementary calcium.

* * * * *